United States Patent
Olds et al.

(10) Patent No.: US 9,554,865 B2
(45) Date of Patent: Jan. 31, 2017

(54) STEADY HAND MICROMANIPULATION ROBOT

(71) Applicant: The Johns Hopkins University, Baltimore, MD (US)

(72) Inventors: Kevin C. Olds, Baltimore, MD (US); Russell H. Taylor, Severna Park, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 252 days.

(21) Appl. No.: 14/540,740

(22) Filed: Nov. 13, 2014

(65) Prior Publication Data

US 2015/0073597 A1     Mar. 12, 2015

Related U.S. Application Data

(63) Continuation of application No. 13/669,176, filed on Nov. 5, 2012, now Pat. No. 8,911,429.

(Continued)

(51) Int. Cl.
*B25J 9/10*       (2006.01)
*B25J 9/00*       (2006.01)
*A61F 9/007*      (2006.01)

(52) U.S. Cl.
CPC .............. *A61B 34/30* (2016.02); *A61B 34/74* (2016.02); *A61B 90/00* (2016.02); *B25J 9/0051* (2013.01);

(Continued)

(58) Field of Classification Search
CPC ......... G06F 17/00; G06B 19/00; A61B 17/00; A61B 19/00; A61B 34/30; A61B 90/00; A61B 34/74; A61B 2090/571; A61B 2034/304; A61F 9/00736; B25J 9/0051; B25J 9/0084; Y10T 74/20335; Y10T 74/20305; Y10S 901/02; Y10S 901/01

(Continued)

(56) References Cited

U.S. PATENT DOCUMENTS 4,976,582 A    12/1990 Clavel
5,020,001 A     5/1991 Yamamoto et al.

(Continued)

FOREIGN PATENT DOCUMENTS

WO    WO-2011/021192 A1    2/2011
WO    WO-2011/025886 A1    3/2011

OTHER PUBLICATIONS

Bonev et al., "Delta Parallel Robot—the Story of Success." http://www.parallemic.org/Reviews/Review002.html. May 2001.

(Continued)

*Primary Examiner* — William Thomson
*Assistant Examiner* — Victor Shapiro
(74) *Attorney, Agent, or Firm* — Venable LLP; Henry J. Daley; George L. Howarah

(57) ABSTRACT

A cooperative-control robot includes a base component, a mobile platform arranged proximate the base component, a translation assembly operatively connected to the base component and the mobile platform and configured to move the mobile platform with translational degrees of freedom substantially without rotation with respect to said the component, a tool assembly connected to the mobile platform, and a control system configured to communicate with the translation assembly to control motion of the mobile platform in response to forces by a user applied to at least a portion of the cooperative-control robot. The translation assembly includes at least three independently operable actuator arms, (Continued)

each connected to a separate position of the mobile platform. A robotic system includes two or more the cooperative-control robots.

23 Claims, 20 Drawing Sheets

Related U.S. Application Data

(60) Provisional application No. 61/555,780, filed on Nov. 4, 2011.

(52) U.S. Cl.
CPC ........ *B25J 9/0084* (2013.01); *A61B 2034/304* (2016.02); *A61B 2090/571* (2016.02); *A61F 9/00736* (2013.01); *Y10T 74/20305* (2015.01); *Y10T 74/20335* (2015.01)

(58) Field of Classification Search
USPC .. 700/245, 247, 258; 606/1, 130; 74/490.01, 490.06; 340/12, 22
See application file for complete search history.

(56) References Cited

U.S. PATENT DOCUMENTS

| | | | |
|---|---|---|---|
| 5,397,323 | A | 3/1995 | Taylor et al. |
| 5,715,729 | A | 2/1998 | Toyama et al. |
| 5,820,623 | A | 10/1998 | Ng |
| 5,887,121 | A | 3/1999 | Funda et al. |
| 6,516,681 | B1 | 2/2003 | Pierrot et al. |
| 6,659,939 | B2 | 12/2003 | Moll et al. |
| 6,836,703 | B2 | 12/2004 | Wang et al. |
| 7,594,912 | B2 | 9/2009 | Cooper et al. |
| 8,113,083 | B2 | 2/2012 | Breu |
| 8,489,235 | B2 | 7/2013 | Moll et al. |
| 8,516,917 | B2 | 8/2013 | Zhao |
| 2005/0216033 | A1 | 9/2005 | Lee et al. |
| 2007/0137374 | A1 | 6/2007 | Schuler et al. |
| 2007/0173976 | A1 | 7/2007 | Schena |
| 2009/0095108 | A1 | 4/2009 | Payandeh et al. |
| 2010/0010504 | A1 | 1/2010 | Simaan et al. |
| 2010/0094312 | A1 | 4/2010 | Ruiz Morales et al. |
| 2010/0139436 | A1 | 6/2010 | Kawashima et al. |
| 2011/0097184 | A1 | 4/2011 | Kinoshita et al. |
| 2011/0154936 | A1 | 6/2011 | Zhao et al. |
| 2012/0182134 | A1 | 7/2012 | Doyle |
| 2014/0066944 | A1* | 3/2014 | Taylor ............... A61B 19/2203 606/103 |

OTHER PUBLICATIONS

Funda et al., "Constrained Cartesian motion control for teleoperated surgical robots", IEEE Transactions on Robotics and Automation, vol. 12-3, pp. 453-466, 1996.
Iordachita et al., "Steady-Hand Manipulator for Retinal Surgery", in MICCAI Workshop on Medical Robotics, Copenhagen, Oct. 5, 2006. pp. 66-73.
Kapoor et al., "A Constrained Optimization Approach to Virtual Fixtures for Multi-Handed Tasks", in IEEE International Conference on Robotics and Automation (ICRA), Pasadena, May 19-23, 2008. pp. 3401-3406.
Kapoor et al., "Simple Biomanipulation Tasks with a "Steady Hand" Cooperative Manipulator", in Proceedings of the Sixth International Conference on Medical Image Computing and Computer Assisted Intervention—MICCAI 2003, Montreal, Nov. 15-18, 2003. pp. 141-148.
Kapoor et al., "Telemanipulation of Snake-Like Robots for Minimally Invasive Surgery of the Upper Airway", in MICCAI Medical Robotics Workshop, Copenhagen, Oct. 2006. pp. 17-25.
Kapoor, Motion Constrained Control of Robots for Dexterous Surgical Tasks, Ph.D. thesis in Computer Science, Johns Hopkins University, Baltimore, 2007.
Kumar et al., "Performance of Robotic Augmentation in Microsurgery-Scale Motions", in 2nd Int. Symposium on Medical Image Computing and Computer-Assisted Surgery, Cambridge, England, Sep. 19-22, 1999. pp. 1108-1115.
Leuth et al. "A surgical robot for maxillofacial surgery." IEEE Industrial Electronics Conference. 1998.
Li et al., "A Constrained Optimization Approach to Virtual Fixtures", in IEEE/RSJ Int Conf on Intelligent Robots and Systems (IROS), Edmonton, Alberta, Canada, 2005, pp. 2924-2929.
Li et al., "Performance of Teleoperated and cooperatively controlled surgical robots with automatically generated spatial virtual fixtures.", in IEEE International Conference on Robotics and Automation, Barcelona, Spain, 2005.
Li et al., "Spatial Motion Constraints in Medical Robot Using Virtual Fixtures Generated by Anatomy", IEEE Transactions on Robotics, vol. 23-1, pp. 4-19, 2007.
Li et al., "Spatial Motion Constraints in Medical Robots Using Virtual Fixtures Generated by Anatomy", in IEEE Conf. on Robotics and Automation, New Orleans, Apr. 2004. pp. 1270-1275.
Li et al., "Telerobot Control by Virtual Fixtures for Surgical Applications". in Advances in Telerobotics Human Interfaces, Bilateral Control and Applications, 2007, pp. 381-401.
Simaan et al., "Design and Integration of a Telerobotic System for Minimally Invasive Surgery of the Throat", Int. J. Robotics Research (special issue on medical robotics), vol. 28-9, pp. 1134-1153, Jun. 2009. http://ijr.sagepub.com/cgi/content/abstract/28/9/1134 DOI 10.1177/0278364908104278, PMC2772168.
Taylor et al., "A Steady-Hand Robotic System for Microsurgical Augmentation", International Journal of Robotics Research, vol. 18-12, 1999.
Tsumaki et al., "Design of a Compact 6-DQF Haptic Interface," Proceedings of the 1998 IEEE International Conference on Robotics & Automation Leuven, Belgium—May 1998.
"Surgical Robotics and Instrumentation" International Journal of Computer Assisted Radiology and Surgery. Jun. 2009; 4 (1): 116-123.
Chinzei et al., "Surgical assist robot for the active navigation in the intraoperative MRI: hardware design issues." Intelligent Robots and Systems, 2000. (IROS 2000). 2000; 1:727-732.
Chinzei et al., "MR Compatible Surgical Assist Robot: System Integration and Preliminary Feasibility Study." Medical Image Computing and Computer-Assisted Intervention—MICCAI 2000. 2000; 921-930.
Kragic et al., "Human-Machine Collaborative Systems for Microsurgical Applications." The International Journal of Robotics Research. Sep. 2005; 24: 731-741.
Miller, "Design and Applications of Parallel Robots." Robotics Research. 2003; 6:161-173.
Mitchell et al., Development and Application of a New Steady-Hand Manipulator for Retinal Surgery, Robotics and Automation, 2007 IEEE International Conference. 2007; 10(14): 623-629.
Nakano et al., "A parallel robot to assist vitreoretinal surgery." International Journal of Computer Assisted Radiology and Surgery. Oct. 2007; 4 (6): 517-526.
Pott et al., "Today's state of the art in surgical robotics." Computer Aided Surgery. 2005; 10 (2): 101-132.

\* cited by examiner

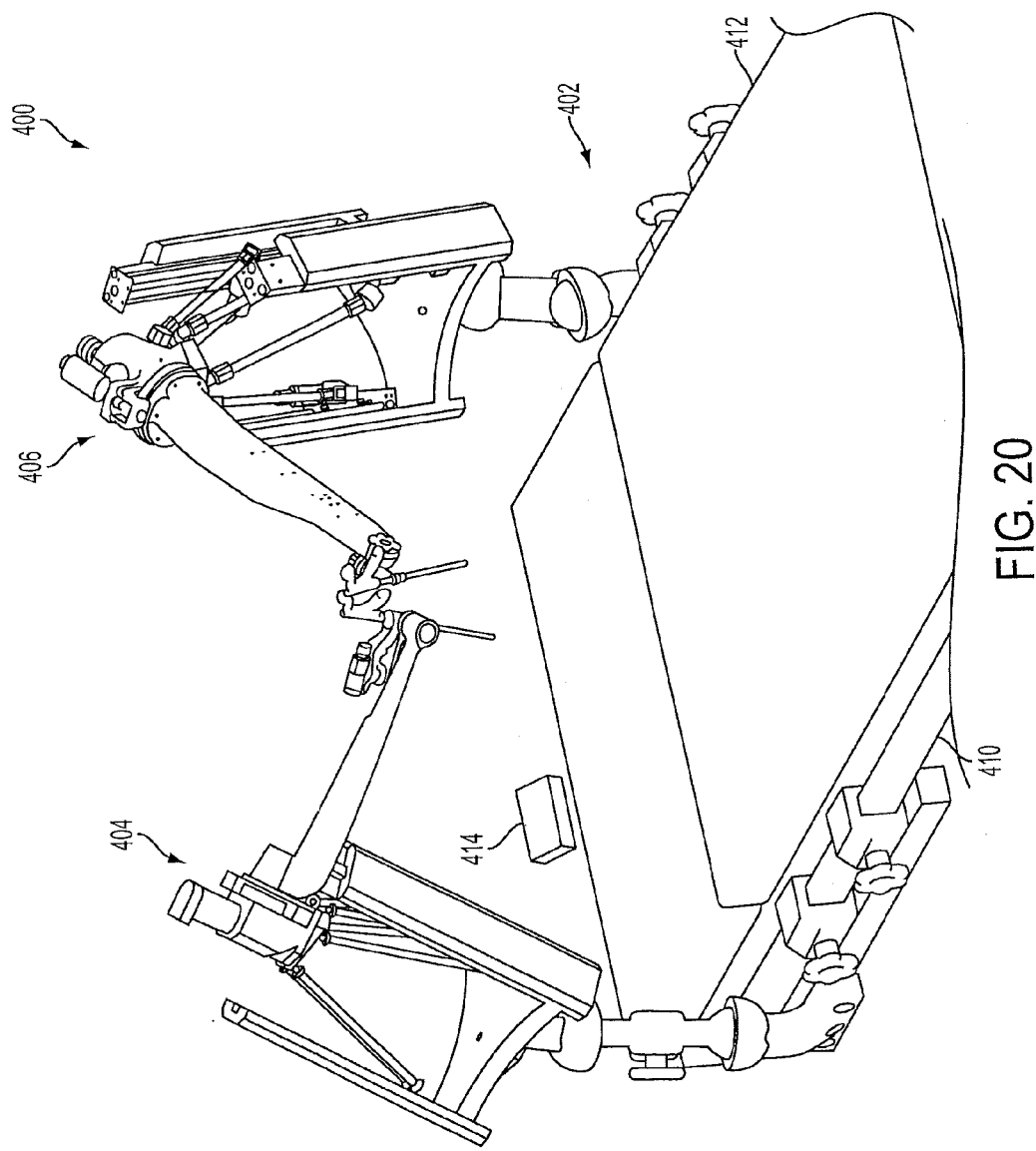

STEADY HAND MICROMANIPULATION ROBOT

CROSS-REFERENCE OF RELATED APPLICATION

This application is a continuation of U.S. application Ser. No. 13/669,176, filed Nov. 5, 2012, which claims priority to U.S. Provisional Application No. 61/555,780 filed Nov. 4, 2011. The entire content of both of these applications are hereby relied upon and incorporated by their reference.

BACKGROUND

1. Field of Invention

The field of the currently claimed embodiments of this invention relates to robotic systems, and more particularly to cooperative-control robots and systems.

2. Discussion of Related Art

Many surgical disciplines such as ophthalmology, otology, laryngology, neurosurgery, and cosmetic and reconstructive surgery, as well as non-surgical fields such as bio-medical research and micro assembly, have a micro manipulation component that pushes human sensory-motor limits. Several robotic solutions have been proposed to solve similar problems in surgery, most prominently the daVinci surgical robot from Intuitive surgical (FIG. 1). The daVinci robot was primarily designed for minimally invasive surgery, and uses a teleoperation control paradigm. This means that the control console and the robot itself are separate pieces of equipment, and the surgeon sits away from the patient.

Though the teleoperation paradigm presents many advantages in minimally invasive surgery, it presents little benefit in many microsurgical tasks. Separating the robot and console causes the whole system to have a much larger operating room (OR) footprint, and unnaturally removes the surgeon from the operation area. The overall bulk of the system makes it time consuming to set up and disengage, so it is difficult to bring it in and out of the OR as needed. Also, since the daVinci robot is designed to mimic the natural hand position of surgeons performing minimally invasive surgery, it has difficulty operating with instrument shafts parallel to each other, as in laryngeal surgery. These limitations can also result in the need to completely change surgical practices in order to accommodate the robot. Another major drawback of this system is its cost. The daVinci robot has both high fixed costs (initial robot cost ~$2 million) and high variable costs (custom disposable surgical instruments, surgical training for daVinci operations).

Since the daVinci robot is mostly used in minimally invasive surgery, it is designed to operate through small incisions. This requires its instruments to pivot about the point where they enter the patient, so as not to put forces on the incision. This is called a remote center of motion (RCM), since the tool is rotating about a point that is outside of the robot. The daVinci robot achieves two rotational degrees of freedom (tilt and roll) about a remote center of motion using a rotation stage and a cable mechanism (FIG. 2). It also has a translational degree of freedom to insert and withdraw tools along the tool axis. This translation mechanism is at the end of the arm, which adds significant bulk and prevents the robot from operating with two instruments parallel to each other and in close proximity (FIG. 3).

Another approach to overcoming human sensorimotor limitations in surgery has been taken by the JHU Eye Robot 2 (FIG. 4). This system uses a cooperative control paradigm where the surgeon sits with the patient and holds the surgical tool along with the robot. The robot senses the surgeon's pressure on the tool through a force sensor and moves accordingly. This system is much smaller and requires less modification to surgical procedures than the daVinci robot.

The JHU Eye Robot 2 uses three translation stages to give x, y, and z translational degrees of freedom, as well as a rotation stage and a remote center of motion linkage[2] to provide the necessary rotational degrees of freedom. If the tool needs to rotate about a point that is different from the rotation center of the mechanisms, then the translation stages can compensate and allow the tool's shaft to rotate about another point. The main limitation of this design is that it relies on a fundamentally serial mechanism, which requires each actuator to carry all subsequent actuators. This makes the overall system larger and heavier than it would otherwise need to be. The weight of the robot imposes speed limits on the translation stages, which in turn prevents them from tracking fast surgical motions, or compensating for centers of motion that are far from that of the mechanism.

An earlier version of the JHU Eye Robot 2, the JHU Eye Robot 1, used a standard 4-bar linkage rather than the remote center of motion linkage, a rotation stage, and a similar 3 degree of freedom (dof) set of translation stages (FIG. 5). The mechanism has no natural RCM point, and uses the translation stages to augment the rotation joints and provide RCM functionality. The RCM linkage was added in the JHU Eye Robot 2 because the translation stages in the serial design were too slow to compensate for the RCM point needed in eye surgery.

Alternative mechanisms for providing three degree of freedom translational motion exist, most notably the delta mechanism (FIG. 6). This mechanism uses three parallelogram linkages in parallel to provide x, y, and z translational degrees of freedom, as well as an extending shaft with two universal joints to provide an additional rotational degree of freedom, for a total of four degrees of freedom. An advantage of this mechanism is that the actuators act in parallel, meaning that they do not need to carry each other's mass. Because of this, the delta mechanism has been used extensively in industrial robotics for high-speed pick and place applications, as well as for surgical applications, and haptic master control (FIG. 7).

The delta mechanism has been used in surgical applications, most notably in maxillofacial surgery (FIG. 8).[6] This system, the ISIS Surgiscope, is a large overhead delta robot designed to manipulate a surgical microscope, which was modified to manipulate surgical tools such as bone drills. It uses a force sensor to detect interaction forces between tools and tissue. Rather than a cooperative control paradigm, this system uses an "interactive planning, programming and teaching" scheme where the robot's freedom is restricted using limits on position, orientation, force, and torque. This system uses motors mounted on the delta robot's mobile platform ((8) in FIG. 6) to control the surgical tools.

This system is not well suited to microsurgery, due to its large size and mass. Also, since it is so large and ceiling mounted, it would not be feasible for two such systems to work together in a bimanual operation. The largely planned and pre-determined operating method this system uses would not be useful in surgeries without extensive preoperative imaging, registration, and rigid anatomy.

The delta mechanism has also been modified to integrate additional actuators into the arms of the system for the purpose of powering additional degrees of freedom at the tip (FIG. 9).[7] A variant of the delta robot which uses linear actuators was also proposed in the original delta robot (FIG. 10). There thus remains the need for improved robots and robotic systems.

SUMMARY

A cooperative-control robot according to an embodiment of the current invention includes a base component, a mobile platform arranged proximate the base component, a translation assembly operatively connected to the base component and the mobile platform and configured to move the mobile platform with translational degrees of freedom substantially without rotation with respect to said the component, a tool assembly connected to the mobile platform, and a control system configured to communicate with the translation assembly to control motion of the mobile platform in response to forces by a user applied to at least a portion of the cooperative-control robot. The translation assembly includes at least three independently operable actuator arms, each connected to a separate position of the mobile platform.

A robotic system according to an embodiment of the current invention includes a support structure, first and second cooperative-control robots connected to the support structure, and a control system adapted to communicate with the first and second cooperative-control robots. Each of the first and second cooperative-control robots includes a base component connected to the support structure, a mobile platform arranged proximate the base component, a translation assembly operatively connected to the base component and the mobile platform and configured to move the mobile platform with translational degrees of freedom substantially without rotation with respect to the base component, and a tool assembly connected to the mobile platform. The control system is configured to control motion of each mobile platform in response to forces by a user applied to at least a portion of a corresponding one of the first and second cooperative-control robots, and each translation assembly includes at least three independently operable actuator arms, each connected to a separate position of the mobile platform.

BRIEF DESCRIPTION OF THE DRAWINGS

Further objectives and advantages will become apparent from a consideration of the description, drawings, and examples.

FIG. 20 is an illustration of a robotic system according to another embodiment of the current invention according to an embodiment of the current invention.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Figure 11:
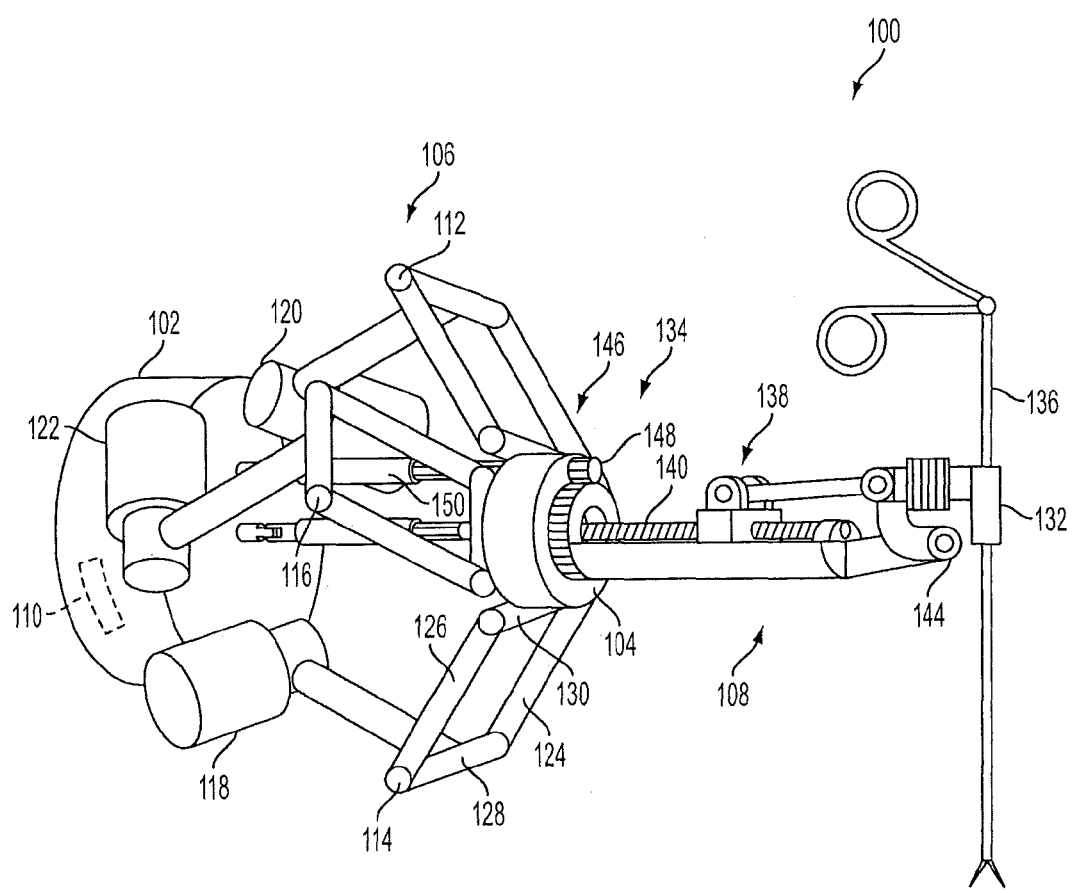
FIG. 11 is an illustration of a cooperative-control robot according to an embodiment of the current invention.

FIG. 11 is a schematic illustration of a cooperative-control robot 100 according to an embodiment of the current invention. The cooperative-control robot 100 includes a base component 102, a mobile platform 104, and a translation assembly 106 operatively connected to the base component 102 and the mobile platform 104.

The base component 102 can be a structural component intended to remain a portion of, and transported with, the cooperative-control robot 100, as illustrated in FIG. 11. However, in other embodiments, it can be a portion of a larger structure, such as a portion of a building. For example, base component could be a ceiling, wall, floor, or beam of a building.

The translation assembly 106 is also configured to move the mobile platform 104 purely with translational degrees of freedom, substantially without rotation with respect to the base component 102. In other words, if the mobile platform 104 is considered to be oriented parallel to the base component 102, it remains substantially parallel as it is move to different positions. The term substantially parallel means that it is within the precision of available manufacturing tolerances and/or to the degree of precision required for the particular application. The mobile platform 104 does not tilt or rotate with respect to the base component 102. In other words, it is constrained in all rotational degrees of freedom. In some embodiments, the mobile platform 104 can be moved with three translational degrees of freedom, which can be represented by mutually orthogonal X, Y and Z coordinates, for example. The base component 102, mobile platform 104 and translation assembly 106 can together be a delta mechanism, such as, but not limited to, any of the above-mentioned delta mechanisms, for example.

The cooperative-control robot 100 further includes a tool assembly 108 connected to the mobile platform 104, and a control system 110 configured to communicate with the translation assembly 106 to control motion of the mobile platform 104 in response to forces by a user applied to at least a portion of the cooperative-control robot 100. The control system 110 is illustrated schematically as being at least partially contained within the base component 102. The control system 110 includes both sensors that can be arranged in multiple positions throughout the cooperative-control robot 100 as well as signal processing components that can be incorporated into the cooperative-control robot 100, such as in the base component 102, and/or a separate component that is either hard wired or in wireless communication with the sensors and translation assembly 106.

The translation assembly 106 includes at least three independently operable actuator arms 112, 114, 116, each of which is connected to a separate position of the mobile platform 104. These at least three actuator arms 112, 114, 116 can be thought of as operating in parallel, in a logical sense, i.e., such as a parallel circuit, rather than in a geometrical sense. In other words, the actuator arms are spaced around the mobile platform 104, and are not cascaded on top of each other such as are the translation stages of the Eye Robot 2.

In some embodiments, translation assembly 106 can further include at least three motors 118, 120 122, each operably connected to a respective one of the at least three independently operable actuator arms 112, 114, 116. The at least three motors 118, 120 122 are supported by the base component 102 such that the mobile platform 104 is free to move without carrying weight of the motors 118, 120 122.

Each of the at least three independently operable actuator arms 112, 114, 116 includes a pair of interconnected structural members (such as pair 124, 126 for actuator arm 114) arranged to form a parallelogram shape (e.g., with cross members 128, 130) which is variable in skewness during operation.

In some embodiments, the at least three independently operable actuator arms 112, 114, 116 can be articulated arms, as is illustrated in FIG. 11. However, not all embodiments require articulated actuator arms. Furthermore, actuator arms can have multiple articulations in other embodiments than that of the example of FIG. 11.

The tool assembly 108 can include a tool holder 132 and a tool rotation assembly 134 operatively connected to the tool holder 132. The tool rotation assembly 134 provides at least two and optionally three rotational degrees of freedom for a tool 136 when held in the tool holder 132. However, the general concepts of the current invention are not limited to the particular tool assembly 108 of FIG. 11. The tool 136 can be an unmodified tool in some embodiments. In some embodiments, the cooperative-control robot 100 can be a surgical robot, such as, but not limited to, a microsurgical robot, and the tool 136 can be an unmodified surgical tool, for example. However, the general concepts of the current invention are not limited to only surgical robots, and are not limited to only unmodified tools.

The tool rotation assembly 134 can include a tilt assembly 138 that has a threaded rod 140 that is operable from the base component 102. As the threaded rod 140 is rotated, the tool holder 132 pivots about the hinge 142. The threaded rod 140 can be driven by a medially located extending spline shaft with universal joints at each end which attaches to the base component 102, and passes through mobile platform 104. In addition, the gear mechanism 146, which is operable from the base component 102, rotates the entire tool assembly 108 except for the threaded rod 140 and gear 148 and rod 150. The gear 148 can be driven by a laterally located extending spline shaft with universal joints at each end which is attached to the base component 102. This is an example in which the tool rotation assembly provides two rotational degrees of freedom. A third rotational degree of freedom can be provided within the tool holder 132, for example, such that the tool 136 rotates about a longitudinal axis. However, the broad concepts of the current invention are not limited to this particular example. For example, different arrangements of the two or three rotational degrees of freedom can be provided and/or more than three rotational degrees of freedom can be provided in other embodiments of the current invention. In an embodiment of the current invention, the at least three articulated arms and the tool rotation assembly are each driven by a respective motor that is connected to the base component. In an embodiment of the current invention, the robotic tool control assembly can further include a force sensor attached to the tool holder to measure at least one force component applied to a tool when held by the tool holder. In an embodiment of the current invention, the force sensor can be a six-degree-of-freedom force sensor. Additional force sensors and/or alternative placements can be provided in other embodiments of the current invention.

In operation, the user grasps the tool 136 to manipulate for surgery, manufacturing or any other suitable manipulation procedure. A couple of examples can include, but are not limited to, microsurgery or micro-precision manufacturing. The one or more force sensors are used to detect forces applied by the user such that the control system 110 causes the mobile platform 104 and tool assembly 108 to be moved in a desired way. For example, motion can be scaled to allow micromanipulation as well being carried out in a smooth manner so as to reduce effects of hand tremor. The control system 110 can include preprogram functions, such as, but not limited to safety zones which cannot be passed, or defined areas of manipulation, for example. The control system 110 can also include a degree of automation, or semi-automation of tasks, for example.

This embodiment can provide an advantage in that all of the motors that control the robot can be located in the base such that none of the motors have to carry any of the other motors. This means that each of the motors is responsible for moving significantly less mass, which allows for smaller motors to be used. It also allows for a reduced mass of the structure that moves the toll assembly. This can result in a much lighter robot that is capable of higher speeds than if a serial mechanism were used.

Figure 12:
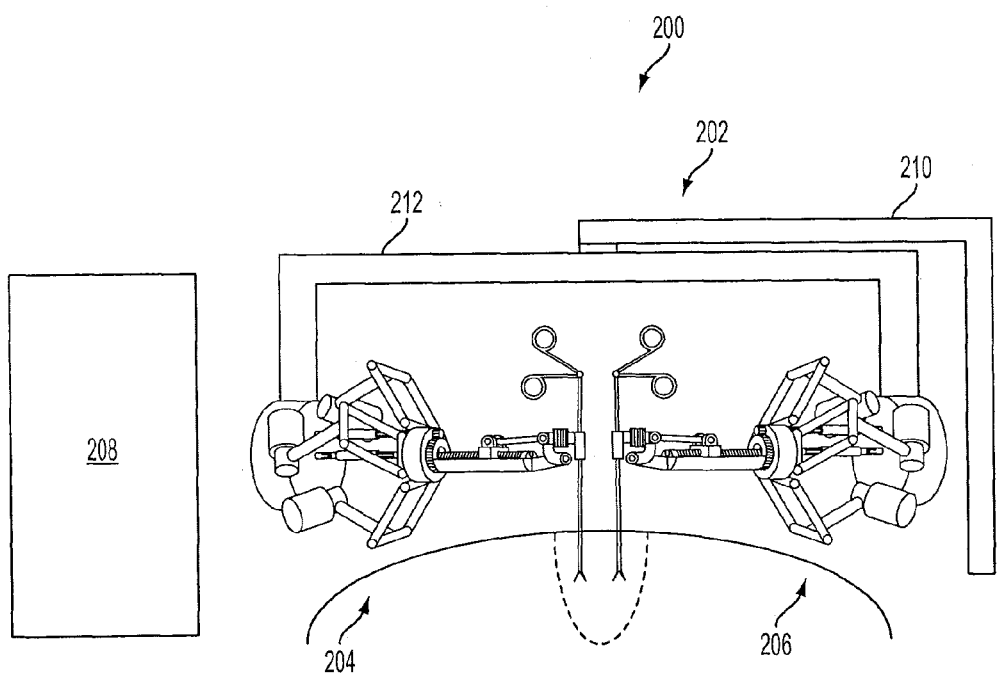
FIG. 12 is a schematic illustration of a robotic system according to an embodiment of the current invention according to an embodiment of the current invention.

FIG. 12 is a schematic illustration of a robotic system 200 according to an embodiment of the current invention. The robotic system 200 includes a support structure 202, first and second cooperative-control robots (204, 206) connected to the support structure 202, and a control system 208 adapted to communicate with the first and second cooperative-control robots (204, 206). Each of the first and second cooperative-control robots 204 and 206, respectively, can be any of the cooperative-control robots according to the current invention. In the example of FIG. 12, the first and second cooperative-control robots 204 and 206 are similar to, or the same as, cooperative-control robot 100.

In the embodiment of FIG. 12, the support structure 202 includes a first overhead boom 210 and a second overhead boom 212 rotatably attached to the first overhead boom 208.

FIG. 12 illustrates how two cooperative-control robots can be arranged such that the tools can be used close together and in a substantially parallel configuration, for example. Although the robotic system 200 is shown with two cooperative-control robots, the general concepts of the current invention are not limited to system with only two cooperative-control robots. For example, robotic systems that have three or more cooperative-control robots can be included in other embodiments.

Figure 13:
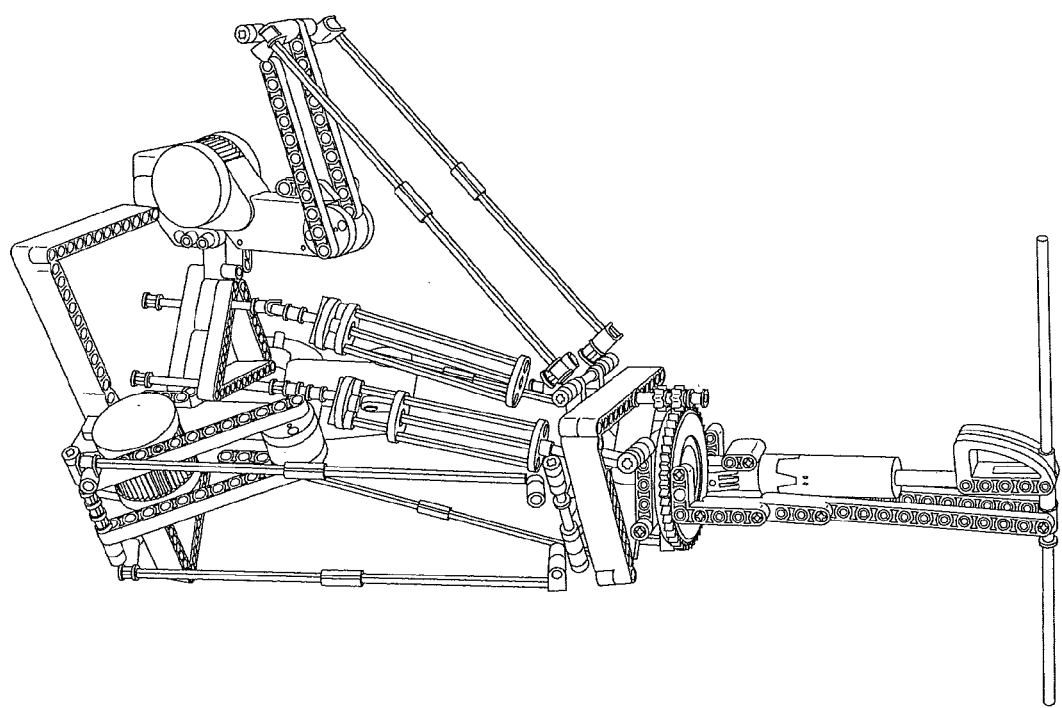
FIG. 13-15 show a prototype of the embodiment of FIG. 11 built with Legos.
Figure 14:
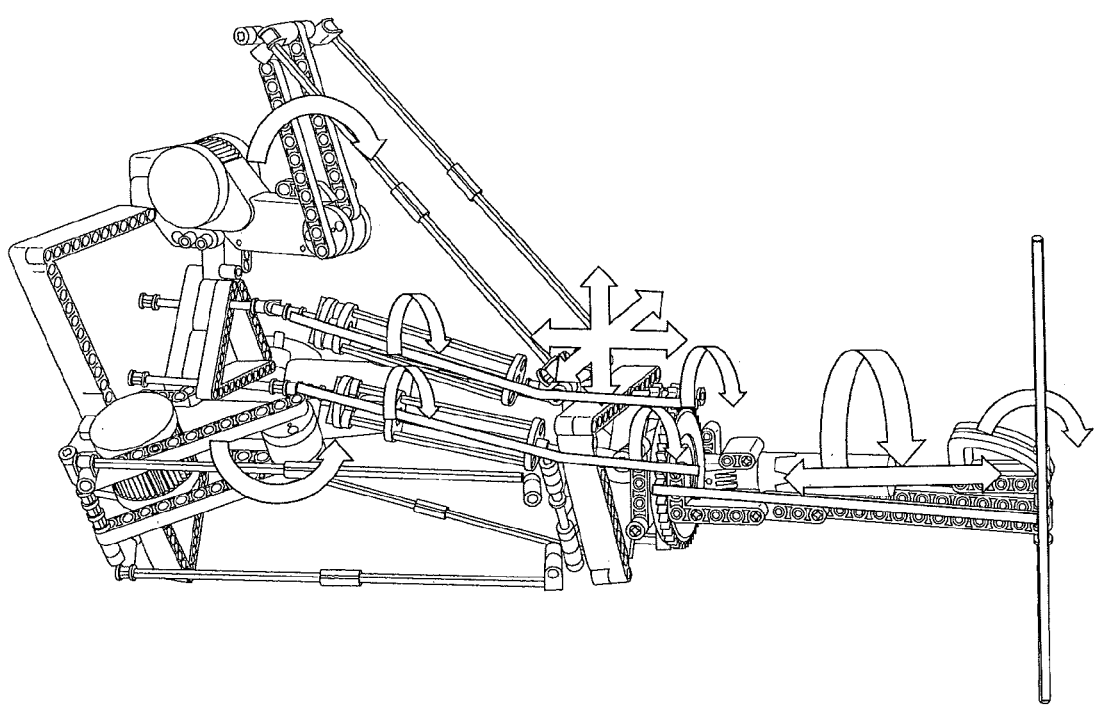
Figure 15:
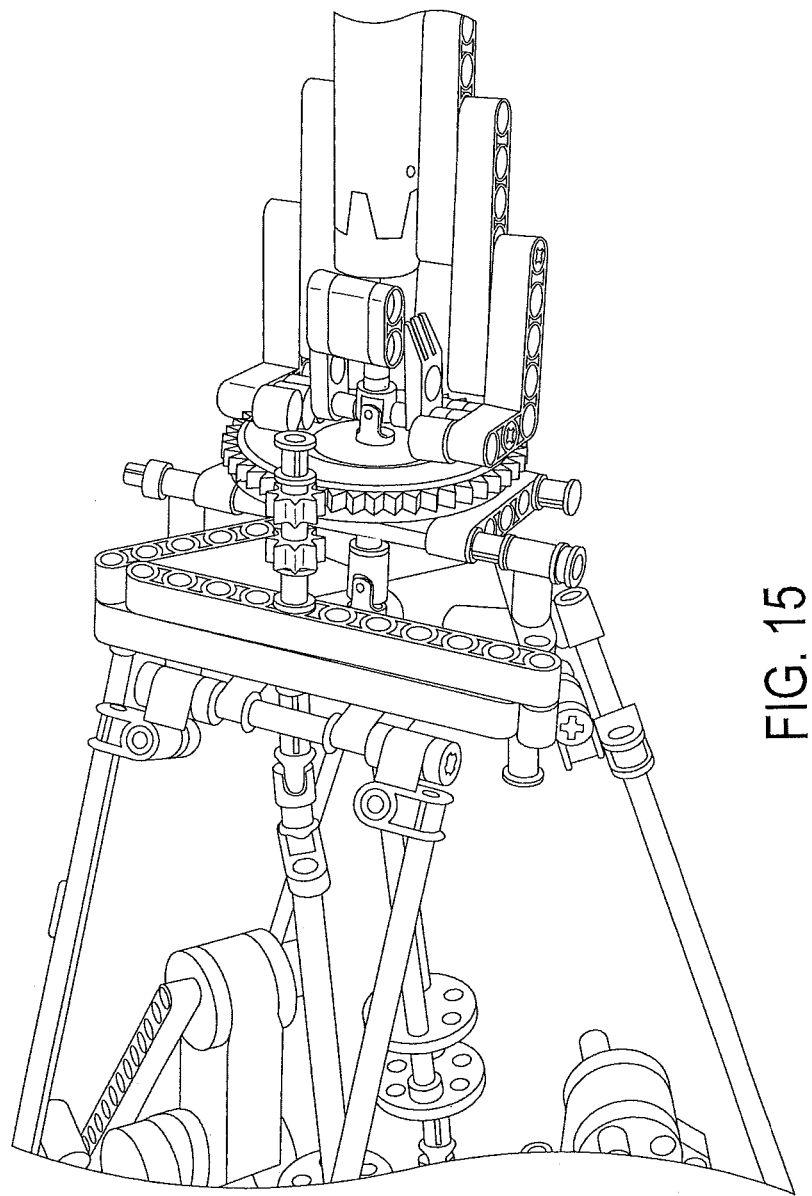
Figure 16:
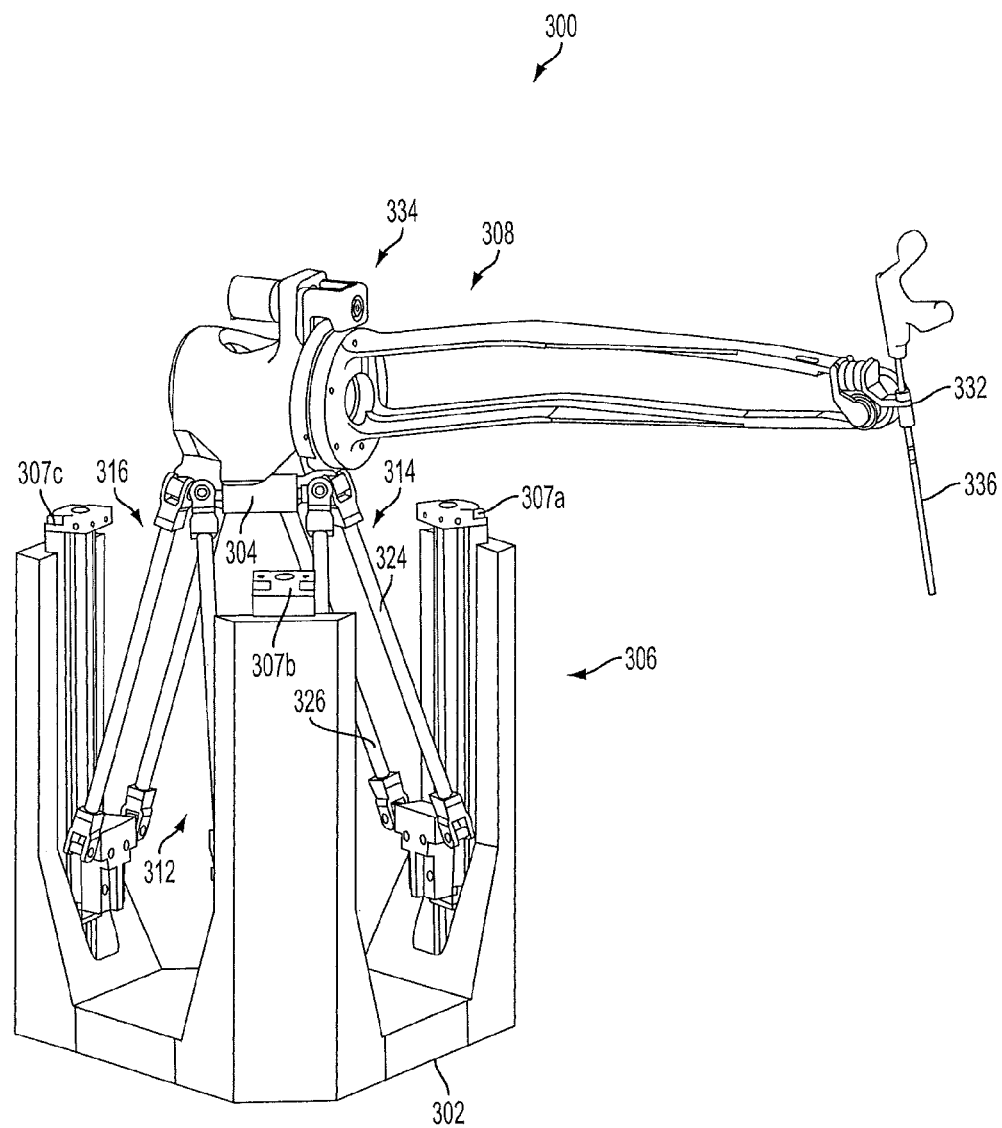
FIGS. 16-19 illustrate a cooperative-control robot according to another embodiment of the current invention.
Figure 17:
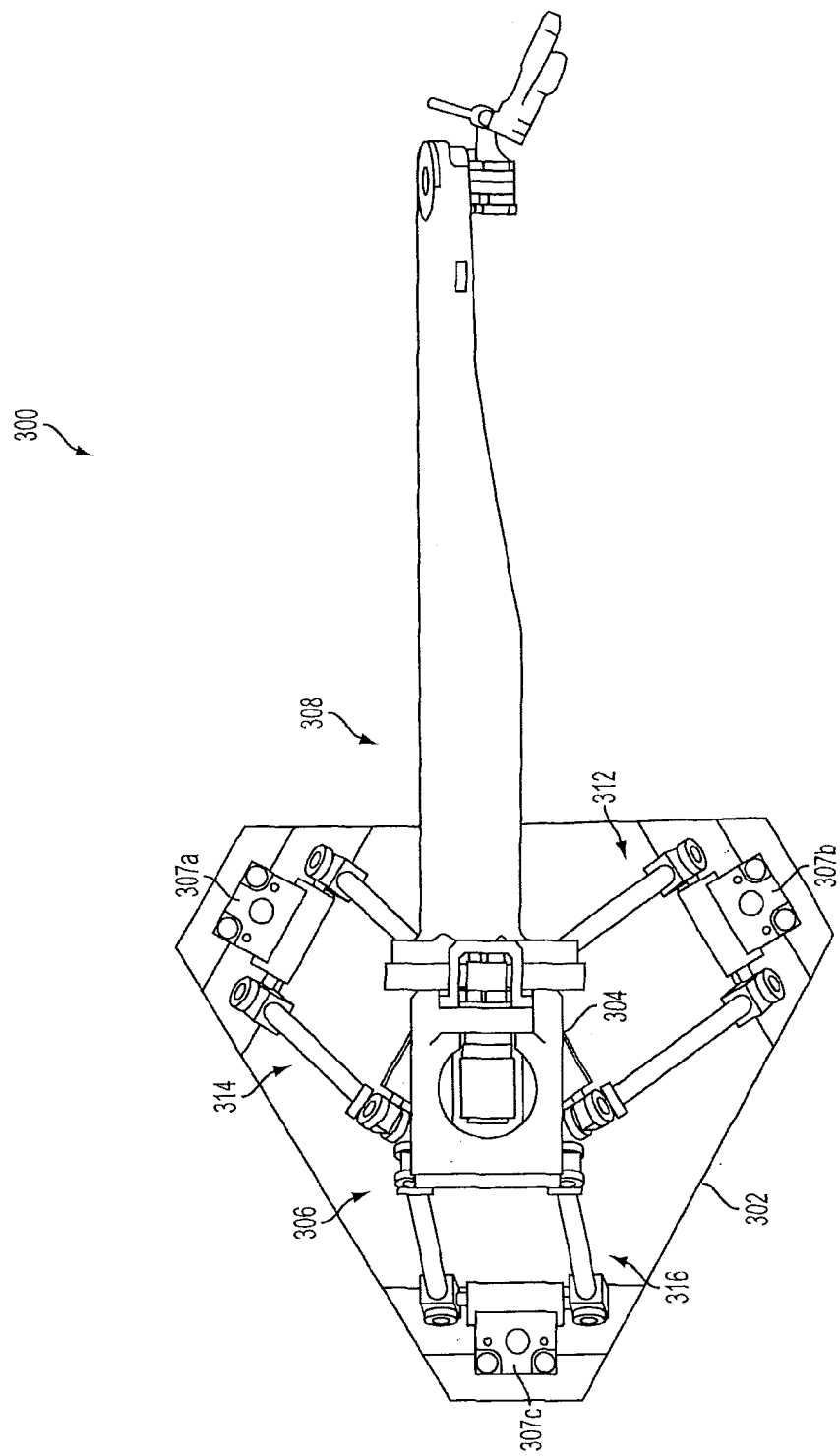
Figure 18:
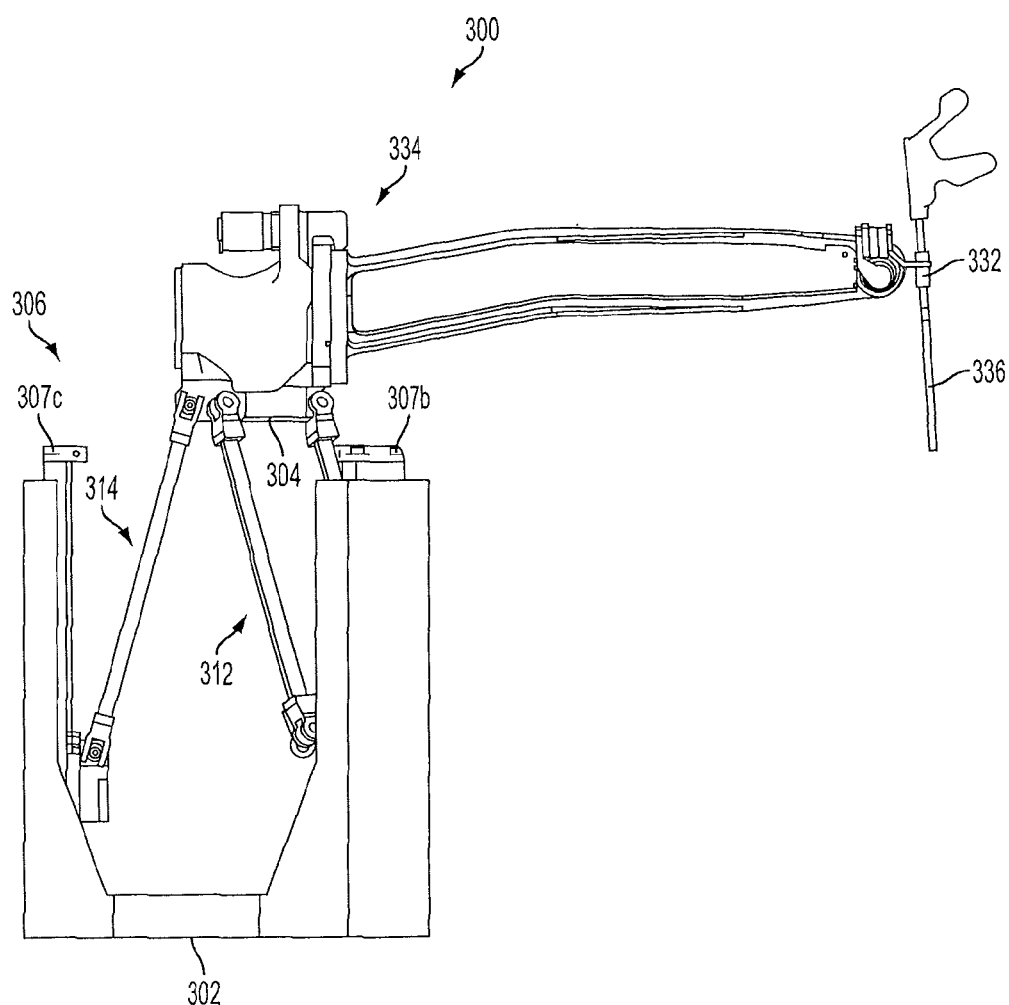
Figure 19:
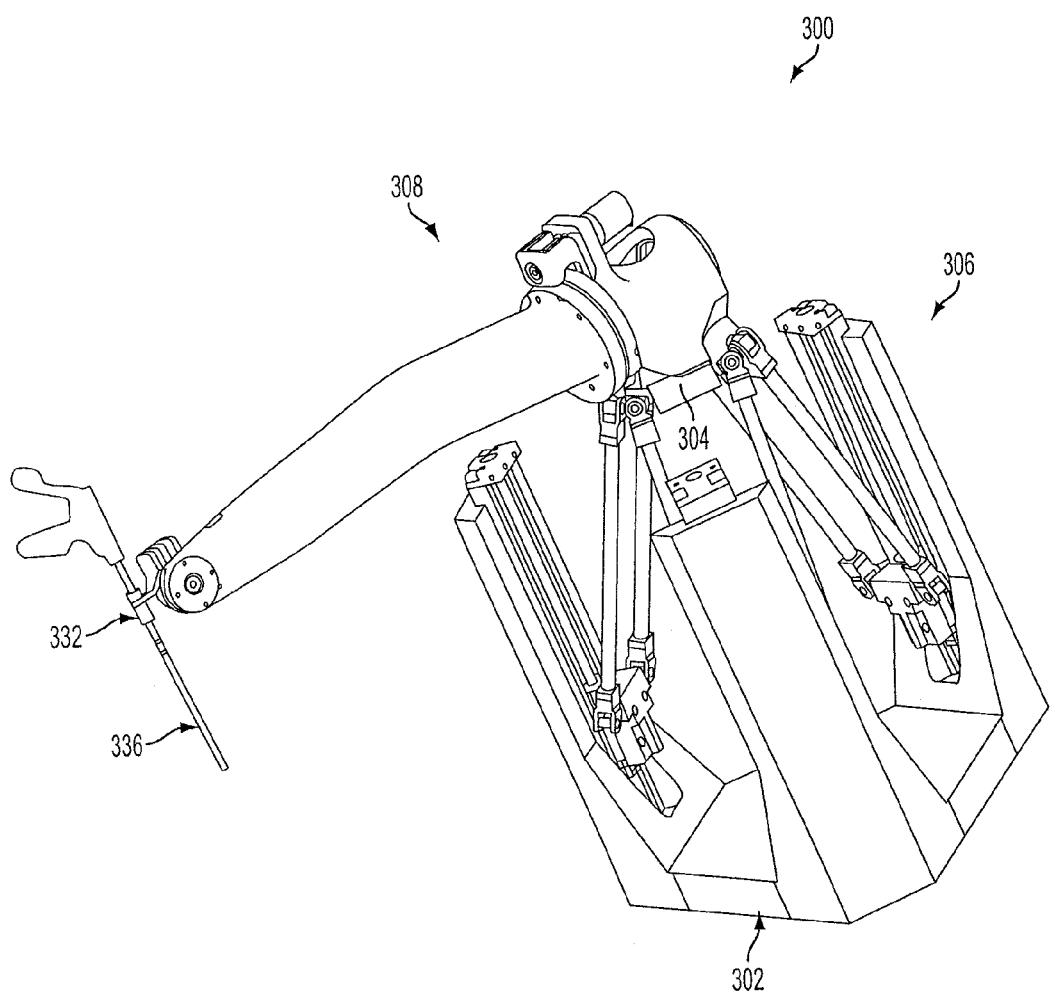

Further embodiments of robotic tool control assemblies and microsurgery robots according to some embodiments of the current invention are described with reference to FIGS. 13-15.

FIGS. 16-19 show three different views of a cooperative-control robot 300 according to another embodiment of the current invention. The cooperative-control robot 300 includes a base component 302, a mobile platform 304 arranged proximate the base component 302, and a translation assembly 306 operatively connected to the base component 302 and the mobile platform 304.

The base component 302 can be a structural component intended to remain a portion of, and transported with, the cooperative-control robot 300, as illustrated in FIGS. 16-19. However, in other embodiments, it can be a portion of a larger structure, such as a portion of a building. For example, base component could be a ceiling, wall, floor, or beam of a building.

The translation assembly 306 is also configured to move the mobile platform 304 purely with translational degrees of freedom, substantially without rotation with respect to the base component 302. In other words, if the mobile platform 304 is considered to be oriented parallel to the base component 302, it remains substantially parallel as it is move to different positions. The term substantially parallel means that it is within the precision of available manufacturing tolerances and/or to the degree of precision required for the particular application. The mobile platform 304 does not tilt or rotate with respect to the base component 302. In other words, it is constrained in all rotational degrees of freedom. In some embodiments, the mobile platform 304 can be moved with three translational degrees of freedom, which can be represented by mutually orthogonal X, Y and Z coordinates, for example.

The translation assembly 306 includes at least three independently operable actuator arms 312, 314, 316, each of which is connected to a separate position of the mobile platform 304. These at least three actuator arms 312, 314, 316 can be thought of as operating in parallel, in a logical sense, i.e., such as a parallel circuit, rather than in a geometrical sense. In other words, the actuator arms are spaced around the mobile platform 304, and are not cascaded on top of each other such as are the translation stages of the Eye Robot 2.

In some embodiments, the translation assembly 306 further includes at least three linear tracks 307a, 307b, 307c arranged such that each of the at least three independently operable actuator arms has an end that is constrained to move along a respective one of the at least three linear tracks 307a, 307b, 307c. In some embodiments, the at least three linear tracks 307a, 307b, 307c can be at least one of attached to, or integral with, the base component 302. The base component 302, mobile platform 304 and translation assembly 306 together can form a linear delta mechanism, for example.

The cooperative-control robot 300 further includes a tool assembly 308 connected to the mobile platform 304, and a control system (not shown) configured to communicate with the translation assembly 306 to control motion of the mobile platform 304 in response to forces by a user applied to at least a portion of the cooperative-control robot 300. The control system in this embodiment can be similar to or substantially the same as described in the embodiment of FIG. 11.

In some embodiments, translation assembly 306 can further include at least three motors (not shown), each operably connected to a respective one of the at least three independently operable actuator arms 312, 314, 316. The at least three motors can be supported by the base component 302 such that the mobile platform 304 is free to move without carrying weight of the motors.

Each of the at least three independently operable actuator arms 312, 314, 316 includes a pair of interconnected structural members (such as pair 324, 326 for actuator arm 314) arranged to form a parallelogram shape (e.g., with cross members) which is variable in skewness during operation.

The tool assembly 308 can include a tool holder 332 and a tool rotation assembly 334 operatively connected to the tool holder 332. The tool rotation assembly 334 provides at least two and optionally three rotational degrees of freedom for a tool 336 when held in the tool holder 332. However, the general concepts of the current invention are not limited to the particular tool assembly 308 of FIG. 16-19. The tool 336 can be an unmodified tool in some embodiments. In some embodiments, the cooperative-control robot 300 can be a surgical robot, such as, but not limited to, a microsurgical robot, and the tool 336 can be an unmodified surgical tool, for example. However, the general concepts of the current invention are not limited to only surgical robots, and are not limited to only unmodified tools.

In operation, the user grasps the tool 336 to manipulate for surgery, manufacturing or any other suitable manipulation procedure. A couple of examples can include, but are not limited to, microsurgery or micro-precision manufacturing. The one or more force sensors are used to detect forces applied by the user such that the control system causes the mobile platform 304 and tool assembly 308 to be moved in a desired way. For example, motion can be scaled to allow micromanipulation as well being carried out in a smooth manner so as to reduce effects of hand tremor. The control system can include preprogram functions, such as, but not limited to safety zones which cannot be passed, or defined areas of manipulation, for example. The control system can also include a degree of automation, or semi-automation of tasks, for example.

In some embodiments, the base component 302 can be configured to attach to a support structure. The support structure can be the same as, or similar to, the support structure 202 of the embodiment of FIG. 12, for example. In other embodiments, the support structure can be one or more bead rails, for example. However, the general concepts of the current invention are not limited to the particular examples of support structures described.

FIG. 20 is an illustration of a robotic system 400 according to another embodiment of the current invention. The robotic system 400 includes a support structure 402, first and second cooperative-control robots (404, 406) connected to the support structure 402, and a control system (not shown) adapted to communicate with the first and second cooperative-control robots (404, 406). Each of the first and second cooperative-control robots 404 and 406, respectively, can be any of the cooperative-control robots according to the current invention. In the example of FIG. 20, the first and second cooperative-control robots 404 and 406 are similar to, or the same as, cooperative-control robot 300.

In the embodiment of FIG. 20, the support structure 402 is an operating bed that includes a first bed rail 410 and a second bed rail 412.

FIG. 20 illustrates another embodiment of two cooperative-control robots arranged such that the tools can be used close together and in a substantially parallel configuration, for example. Although the robotic system 400 is shown with two cooperative-control robots, the general concepts of the current invention are not limited to system with only two cooperative-control robots. For example, robotic systems that have three or more cooperative-control robots can be included in other embodiments.

In some embodiments of robotic systems according to the current invention, can further include a user input device adapted to communicate with the control system to at least one of interrupt or supplement cooperative control. For example, the robotic system 400 can include a user input device 414 in some embodiments. The user input device 414 can be, but is not limited to, a foot peddle, for example.

As described above, some embodiments of the current invention include two cooperative-control robots. The cooperative-control robots can be positioned so that a surgeon can operate one with both hands, thus providing bimanual surgical capability. In some embodiments, the system could include a hands-on cooperative control paradigm, similar to the JHU "steady hand" robots. In this case, a force sensor attached to the tool holder, or to a control handle attached to the tool holder or to the surgical tool itself, would sense forces exerted by the surgeon on the tool, and the robot controller would cause the robot to move to comply with these forces. In this case, the surgeon can have the impression that he or she is manipulating the tool in much the same way as in normal surgery. But since the robot is doing the actual moving of the tool, there will be no, or at least substantially reduced, hand tremor. Also, if the surgeon releases the tool, the tool can simply stop moving, rather than fall as it would in normal surgery.

The robotic systems according to some embodiments may also be teleoperated from master control arms such as those used to control the DaVinci surgical robot or from simpler master control arms such as the Sensable Technology Omni arms, or from multiple joysticks, or from other master control arms. In this case, forces exerted on the tools sensed in the force sensors can be "fed back" to the master control arms to provide haptic feedback or to otherwise modify the motion of the robot. Also, the control modes may be mixed or switched between teleoperation control and hands-on cooperative control.

In addition, the robots may be programmed to perform simple motions under semi-autonomous or supervised control. In this case, the surgeon would manipulate one or both tools to achieve a desired tool-to-tissue relationship and then instruct the robot to make one or more motions autonomously, within a constrained volume, while the surgeon supervises. An example of this behavior might be precise insertion of a needle or injection device a fixed (small) distance into tissue, stopping if a sensor exceeds a threshold value.

Cooperative control refers to the way the steady hand robots are controlled. Both the surgeon and the robot hold the tool (or the surgeon holds a handle attached to the tool handle). The robot senses forces exerted by the surgeon and moves to comply with the motion. The following references describe some general concepts of cooperative control, all of which are incorporated herein by reference:

R. Kumar, T. Goradia, A. Barnes, P. Jensen, L. Whitcomb, D. Stoianovici, L. Auer, and R. Taylor, "Performance of Robotic Augmentation in Microsurgery-Scale Motions", in 2nd Int. Symposium on Medical Image Computing and Computer-Assisted Surgery, Cambridge, England, Sep. 19-22, 1999. pp. 1108-1115.

R. H. Taylor, P. Jensen, L. L. Whitcomb, A. Barnes, R. Kumar, D. Stoianovici, P. Gupta, Z. X. Wang, E. deJuan, and L. R. Kavoussi, "A Steady-Hand Robotic System for Microsurgical Augmentation", International Journal of Robotics Research, vol. 18-12, 1999.

Kapoor, R. Kumar, and R. Taylor, "Simple Biomanipulation Tasks with a "Steady Hand" Cooperative Manipulator", in Proceedings of the Sixth International Conference on Medical Image Computing and Computer Assisted Intervention—MICCAI 2003, Montreal, Nov. 15-18, 2003. pp. 141-148.

Iordachita, A. Kapoor, B. Mitchell, P. Kazanzides, G. Hager, J. Handa, and R. Taylor, "Steady-Hand Manipulator for Retinal Surgery", in MICCAI Workshop on Medical Robotics, Copenhagen, Oct. 5, 2006. pp. 66-73.

Any of the control modes described above may be modified by "virtual fixtures" to further constrain the motion of the robots. These "virtual fixtures" can be derived from kinematic constraints (e.g., to implement a "virtual remote-center-of-motion" for a tool. Further discussion of methods for providing such virtual fixtures may be found in the following references, all of which are incorporated herein by reference:

J. Funda, R. Taylor, B. Eldridge, S. Gomory, and K. Gruben, "Constrained Cartesian motion control for teleoperated surgical robots", IEEE Transactions on Robotics and Automation, vol. 12-3, pp. 453-466, 1996.

U.S. Pat. No. 5,887,121, J. Funda and R. H. Taylor, "Method of constrained Cartesian control of robotic mechanisms with active and passive joints", Filed Filed Feb. 18, 1999, Issued May 1, 2001.

M. Li and R. H. Taylor, "Spatial Motion Constraints in Medical Robots Using Virtual Fixtures Generated by Anatomy", in IEEE Conf. on Robotics and Automation, New Orleans, April, 2004. pp. 1270-1275.

M. Li, A. Kapoor, and R. Taylor, "A Constrained Optimization Approach to Virtual Fixtures", in IEEE/RSJ Int Conf on Intelligent Robots and Systems (IROS), Edmonton, Alberta, Canada, 2005, pp. 2924-2929

M. Li and R. H. Taylor, "Performance of Teleoperated and cooperatively controlled surgical robots with automatically generated spatial virtual fixtures.", in IEEE International Conference on Robotics and Automation, Barcelona, Spain, 2005

A. Kapoor, N. Simaan, and R. H. Taylor, "Telemanipulation of Snake-Like Robots for Minimally Invasive Surgery of the Upper Airway", in MICCAI Medical Robotics Workshop, Copenhagen, October, 2006. pp. 17-25.

M. Li, M. Ishii, and R. H. Taylor, "Spatial Motion Constraints in Medical Robot Using Virtual Fixtures Generated by Anatomy", IEEE Transactions on Robotics, vol. 23-1, pp. 4-19, 2007.

M. Li, A. Kapoor, and R. H. Taylor, "Telerobot Control by Virtual Fixtures for Surgical Applications". in Advances in Telerobotics Human Interfaces, Bilateral Control and Applications, M. Ferre, M. Buss, R. Aracil, C. Melchiorri, and C. Balaguer, Eds., 2007, pp. 381-401.

A. Kapoor, Motion Constrained Control of Robots for Dexterous Surgical Tasks, Ph.D. thesis in Computer Science, Johns Hopkins University, Baltimore, 2007.

A. Kapoor and R. Taylor, "A Constrained Optimization Approach to Virtual Fixtures for Multi-Handed Tasks", in IEEE International Conference on Robotics and Automation (ICRA), Pasadena, May 19-23, 2008. pp. 3401-3406.

N. Simaan, K. Xu, A. Kapoor, W. Wei, P. Kazanzides, P. Flint, and R. Taylor, "Design and Integration of a Telerobotic System for Minimally Invasive Surgery of the Throat", Int. J. Robotics Research (special issue on medical robotics), vol. 28-9, pp. 1134-1153, June, 2009. http://ijr.sagepub.com/cgi/content/abstract/28/9/1134 DOI 10.1177/0278364908104278, PMC2772168.

Standard surgical instruments could be fitted with adapters so that they could be quickly inserted into and removed from the robot's instrument holder. Some embodiments of the current invention can use carbon fiber, aluminum, and other stiff, lightweight materials, for example. The three translation-driving motors can be implemented using DC servomotors with optical encoders and harmonic gearheads to minimize backlash, for example. The tilt degree of freedom could be implemented using a low backlash screw-based mechanism such as a ball-screw. The roll degree of freedom can be coupled to the drive shaft using a low backlash gear ratio reduction mechanism such as a timing belt, or a chain, for example. If additional reduction is needed, a small harmonic gear box may be used at the end of the drive shaft. The drive shafts can be implemented using spline couplings or ball splines to minimize backlash. Universal joints with needle bearings capable of operating at at least 30 degrees of deflection can be used on the ends of the drive shafts.

In other embodiments, it can also be possible to remotely teleoperate the system using a master such as the daVinci console or locally teleoperate it using simpler devices such as a Phantom Omni or joystick. In this case, it can be possible to use the built-in force sensor to provide force feedback of tool forces to the surgeon.

In other embodiments, it can also be possible to integrate custom high-dexterity instruments, such as the wristed instruments that the daVinci system uses, rather than existing surgical instruments.

In other embodiments, more degrees of freedom can be added using additional drive shafts, small motors directly on the end effector, or some other power transmission method, such as pneumatics, for example.

The drive shafts can be configured in other ways, such as with two concentric shafts, or both drive shafts off center coupled with chains, belts or cables to the tilt/roll mechanisms.

Other power transmission methods from shafts to the tilt/roll mechanisms can be used (chains, gears, cables, belts, etc.).

The tilt mechanism can be implemented in many ways, such as a 4-bar linkage driven by a linear actuator as illustrated in the drawings, a linkage driven by a rotary actuator, or directly driven by a rotary actuator using a chain, cable, pulley, or other coupling. A remote center of motion linkage such as in the Eye Robot 2 can also be used.

In other embodiments, additional robotic tool control assemblies can be added to provide robotic assistance to more than one user, or to provide control of more instruments for one user.

An additional robot can be added to control a visualization device, such as a flexible or rigid endoscope.

Figure 1:
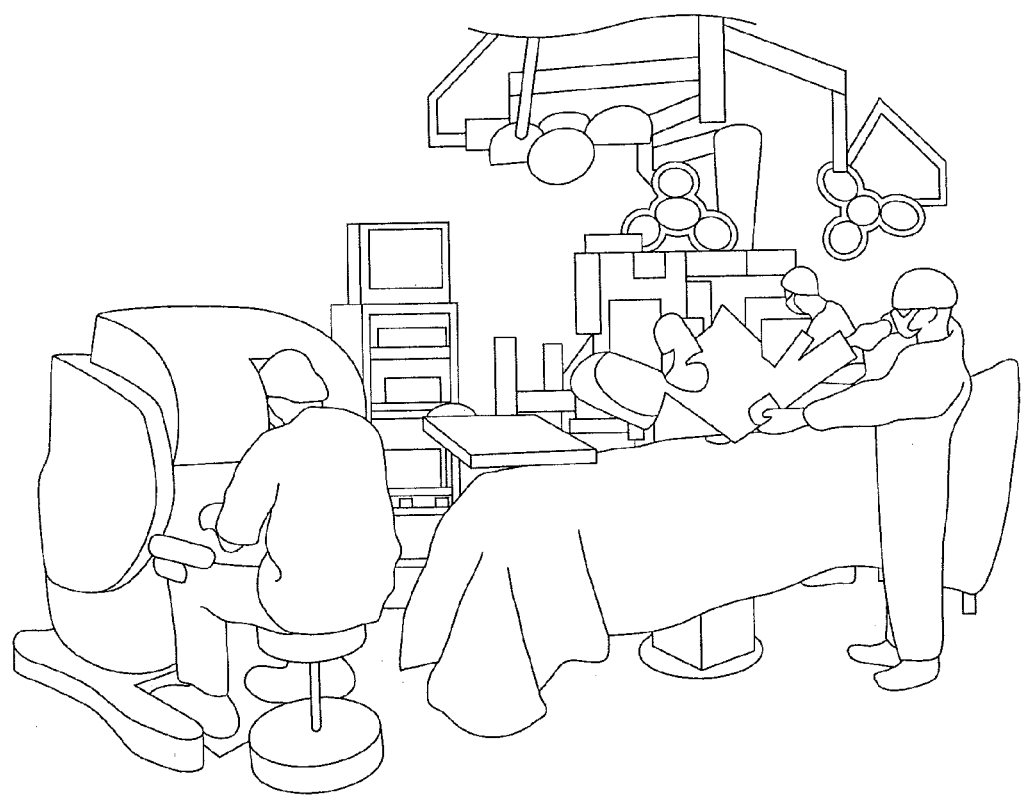
FIG. 1 shows an example of the daVinci robotic system from Intuitive Surgical.
Figure 2:
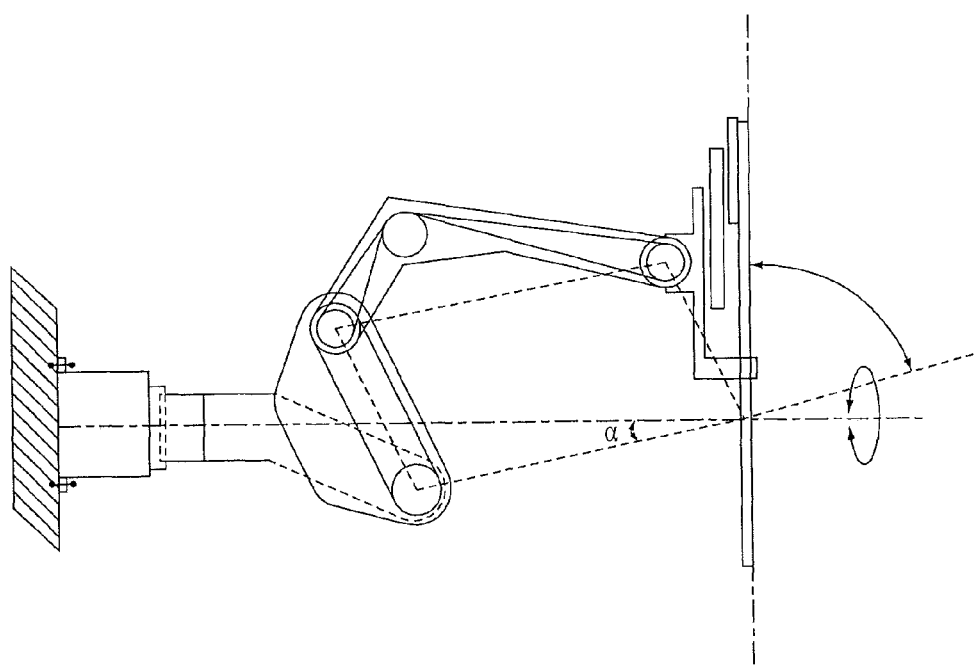
FIG. 2 illustrates the daVinci remote center of motion mechanism[1].
Figure 3:
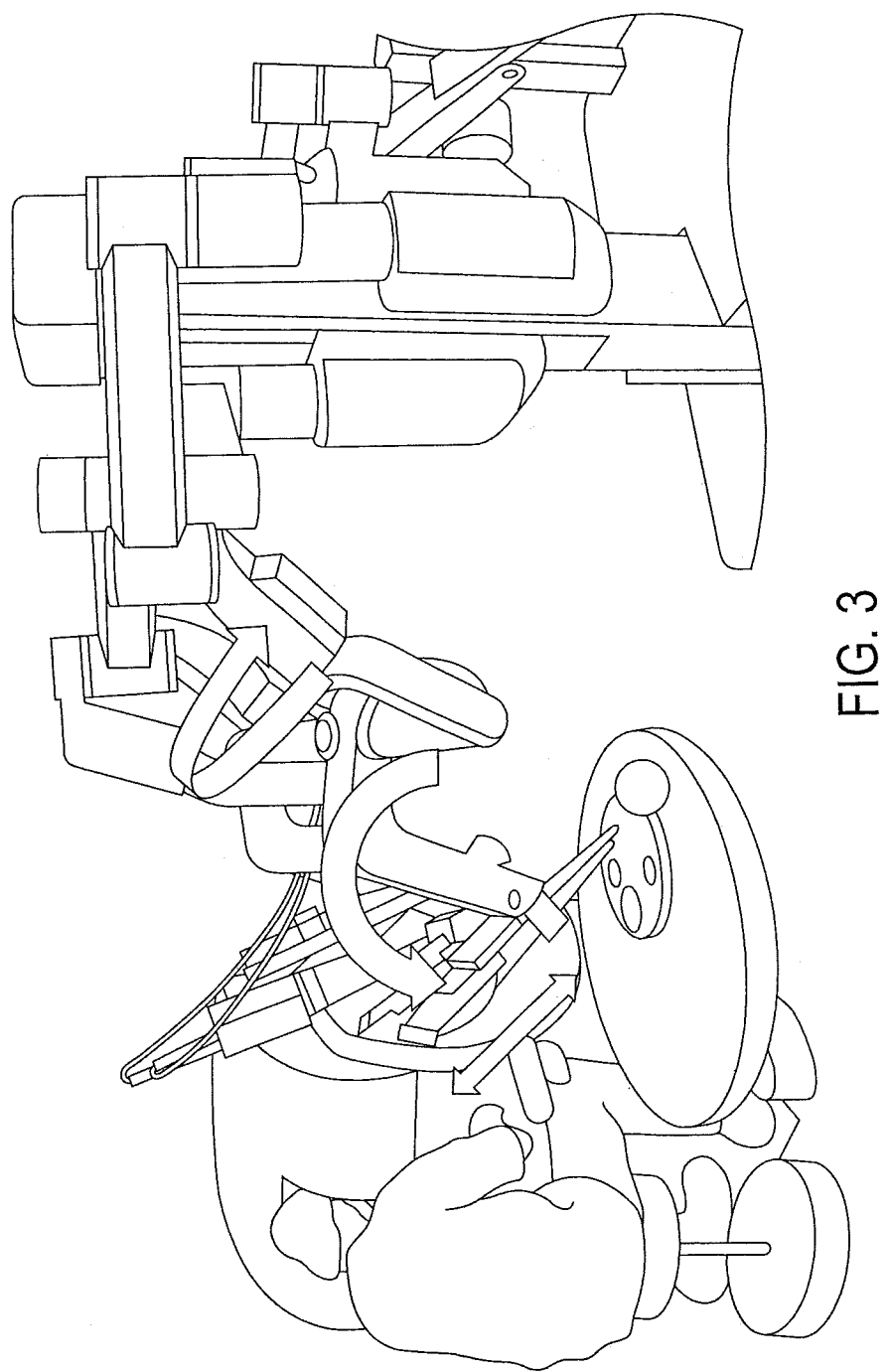
FIG. 3 shows an example of the daVinci degrees of freedom. (Light, straight, two-headed arrow: insertion/extraction translation stage. Shaded, lower, curved arrow: Tilt. Dark, upper, curved arrow: Roll.)
Figure 4:
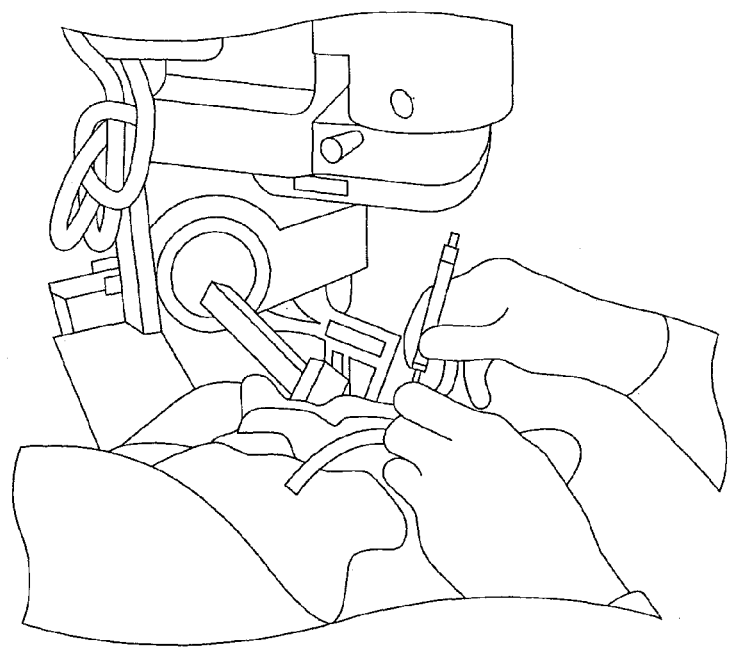
FIG. 4 shows an example of the JHU Eye Robot 2.
Figure 4:
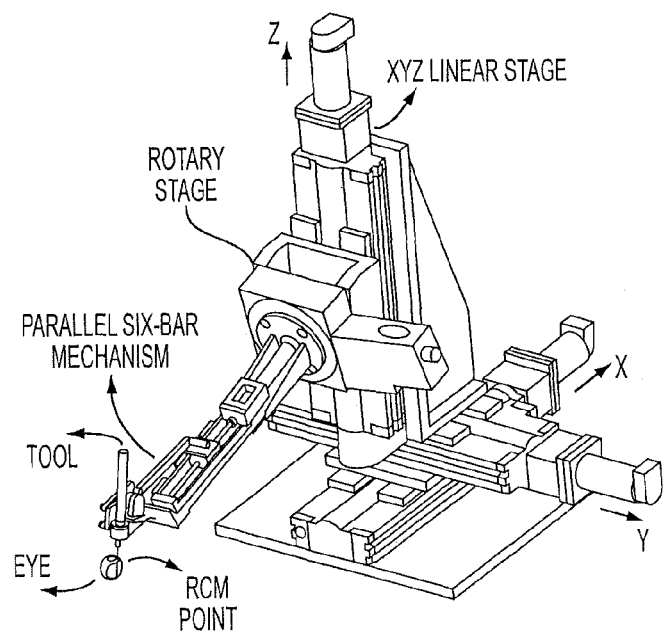
Figure 5:
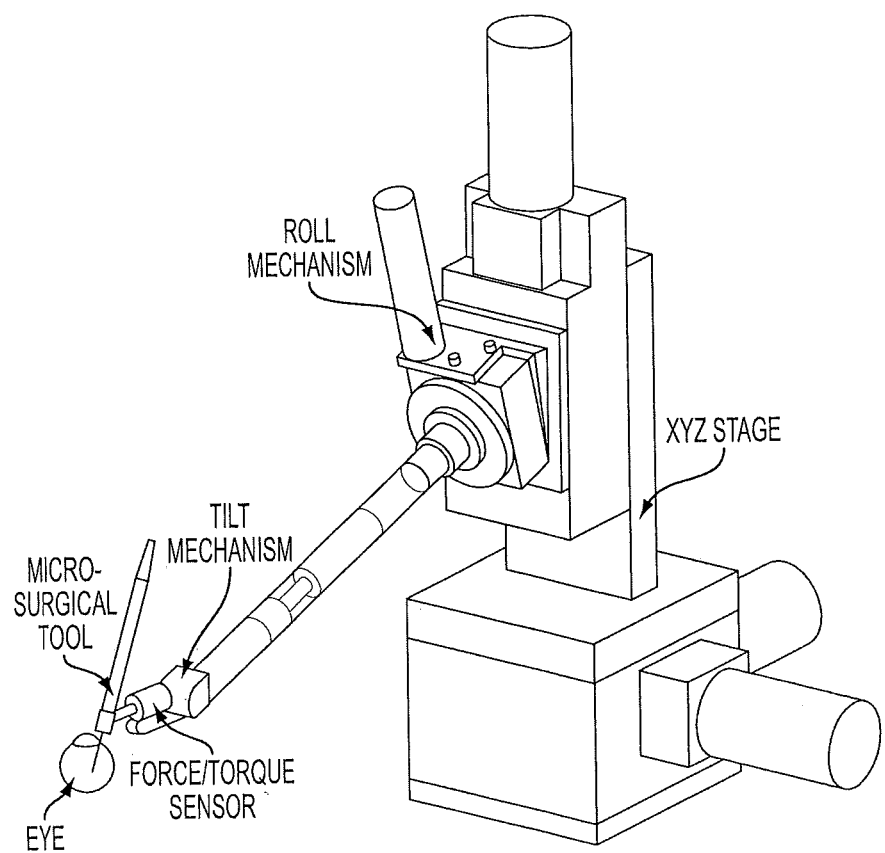
FIG. 5 shows an example of the JHU Eye Robot 1.
Figure 6:
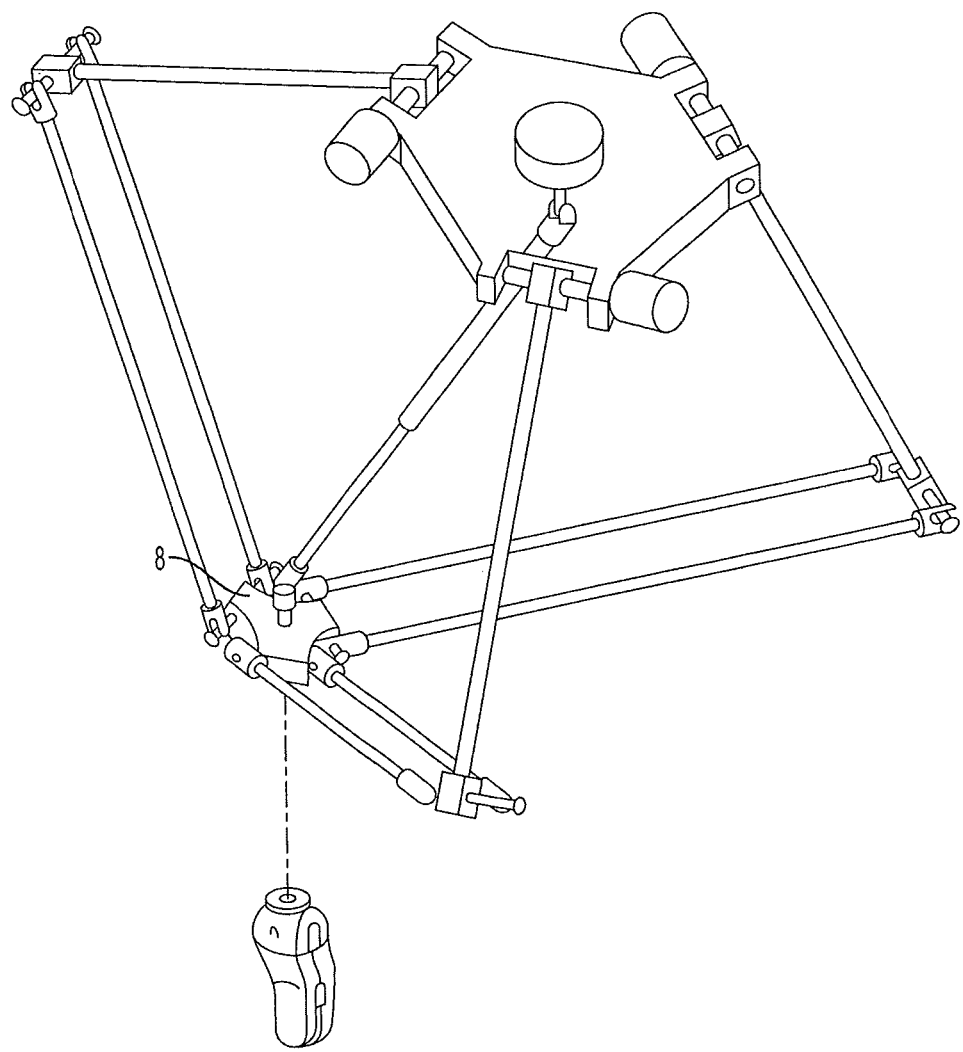
FIG. 6 is a drawing of a delta mechanism[3].
Figure 7:
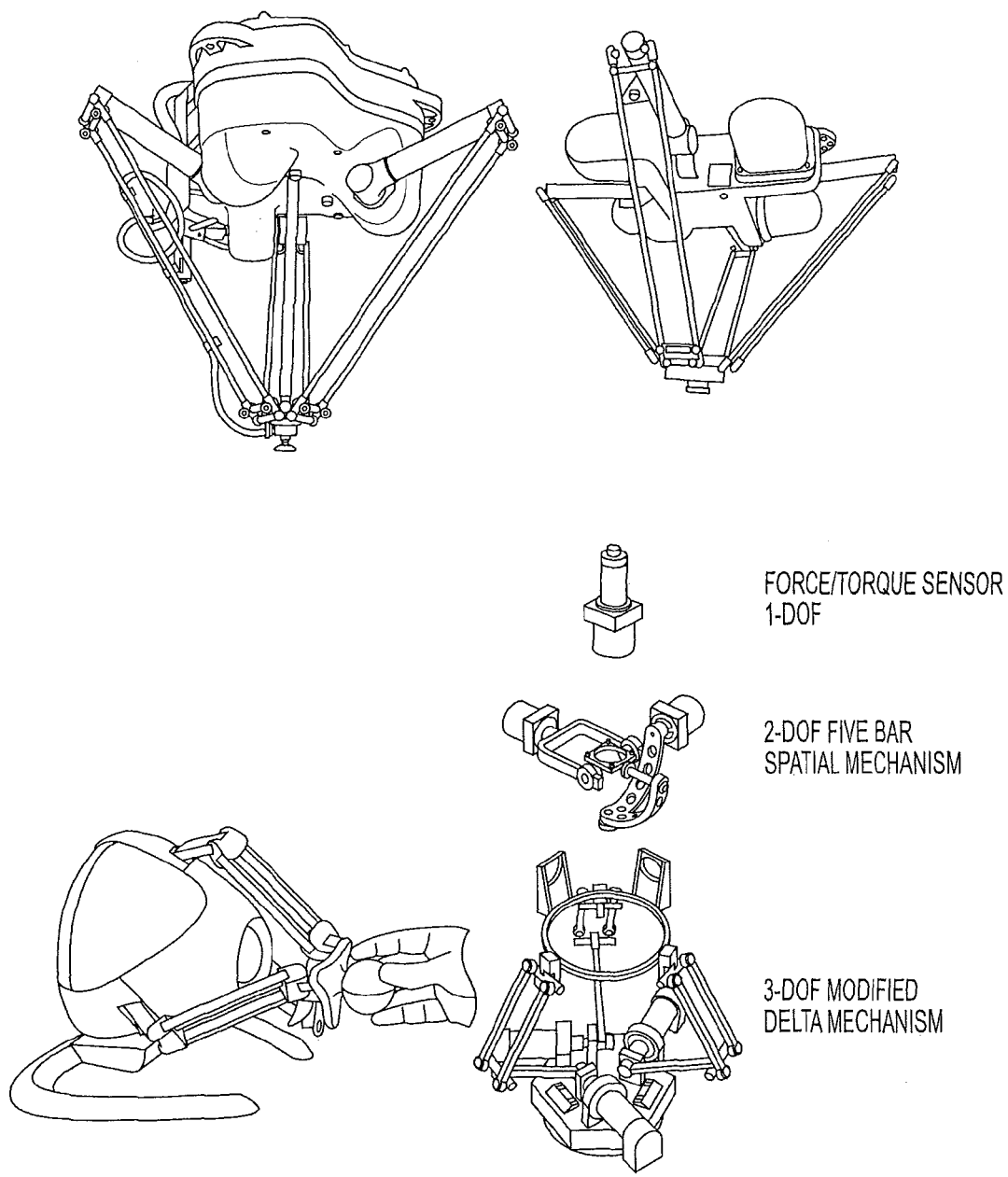
FIG. 7 shows examples of: Top Left, Industrial delta robot[4]; Top Right, The Adept Quattro, a four link delta robot; Bottom Left, Commercial haptic master using delta mechanism; Bottom Right, 6 dof haptic master.[5]
Figure 8:
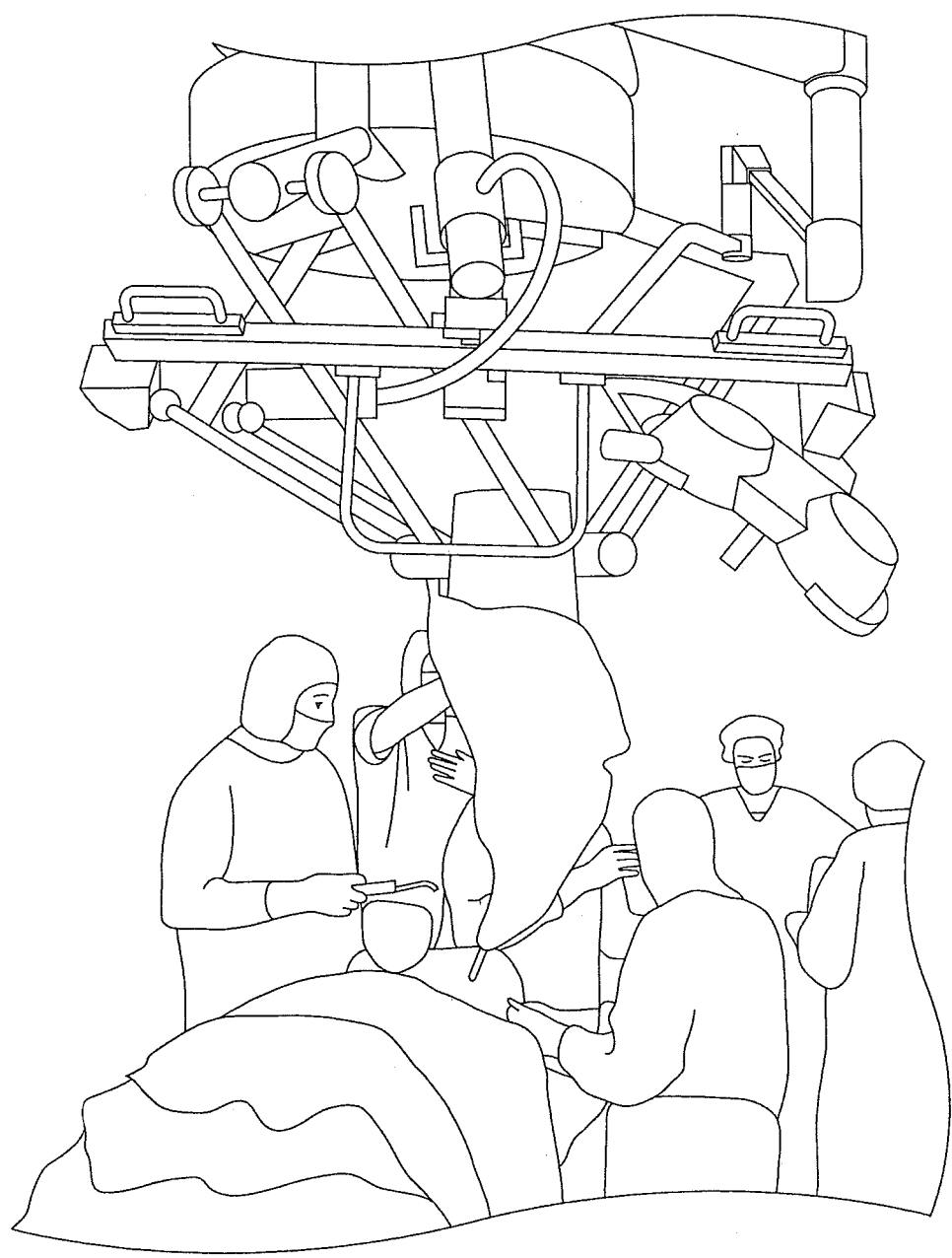
FIG. 8 show an example a delta robot for maxillofacial surgery.
Figure 9:
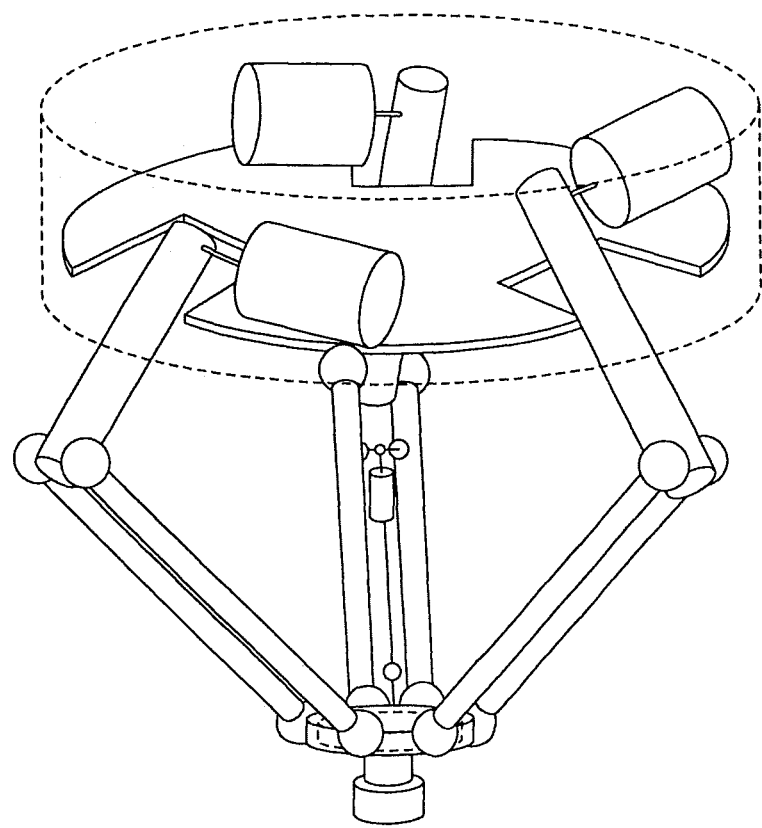
FIG. 9 is a schematic illustration of a modified delta mechanism with three actuators mounted on the robot's legs.
Figure 10:
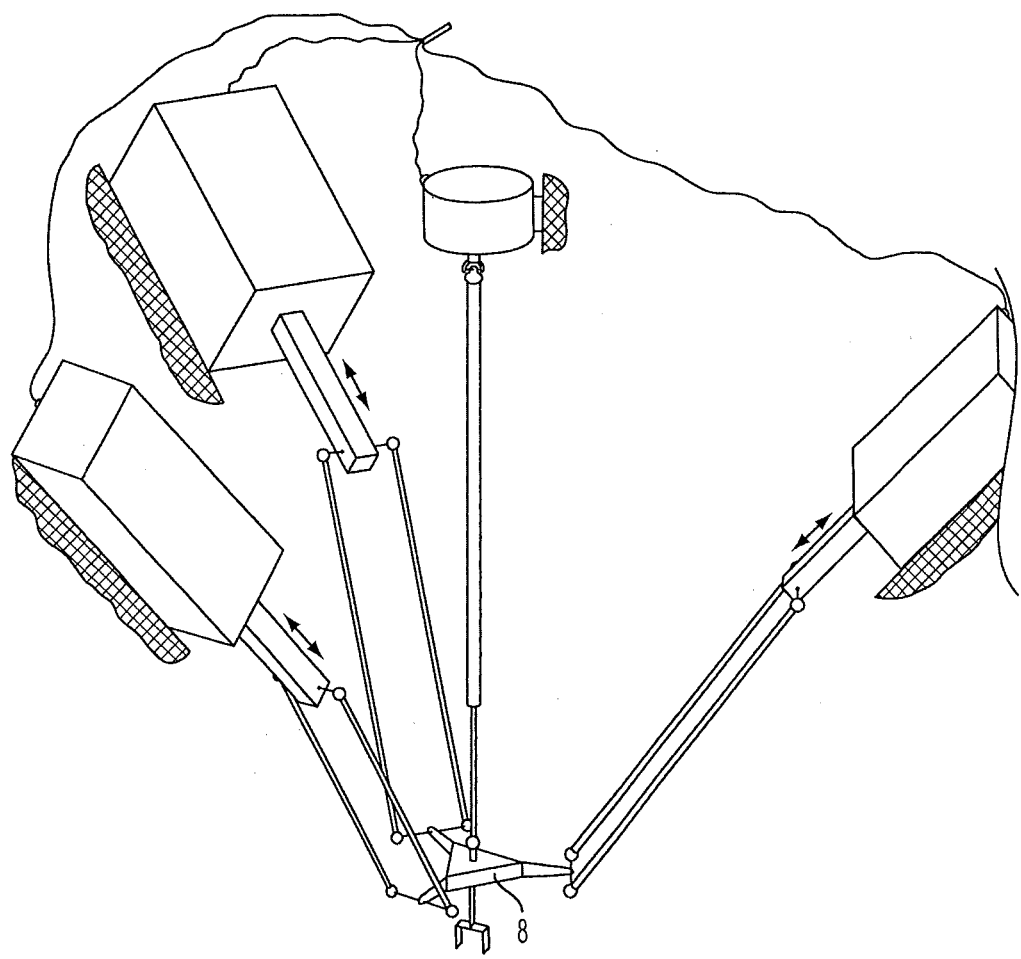
FIG. 10 is an illustration of a linear variant of the delta robot.[3]

For added rigidity, it would also be possible to implement the delta mechanism in the actuators with four links, as in the Adept Quattro (FIG. 7 Mid Left).

Depending on the application, it may be geometrically advantageous to use the linear variant of the delta mechanism in the robots.

REFERENCES

1. Cooper et al. "Offset remote center manipulator for robotic surgery." U.S. Pat. No. 7,594,912. 29 Sep. 2009.
2. Taylor, Russell et al. "Remote center-of-motion robot for surgery." U.S. Pat. No. 5,397,323. 30 Oct. 1992.
3. Clavel, Reymond. "Device for the movement and positioning of an element in space." U.S. Pat. No. 4,976,582. 11 Dec. 1990.
4. Man Bonev. "Delta Parallel Robot—the Story of Success." http://www.parallemic.org/Reviews/Review002.html. May 2001.
5. Y. Tsumaki, H. Naruse, D. N. Nenchev, and M. Uchiyarna. Design of a Compact 6-DQF Haptic Interface. Proceedings of the 1998 IEEE International Conference on Robotics & Automation Leuven, Belgium—May 1998
6. Leuth et al. "A surgical robot for maxillofacial surgery." IEEE Industrial Electronics Conference. 1998.
7. Kinoshita et al. "Parallel Link Robot." US Patent 2011/0097184 A1. Apr. 28, 2011.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A cooperative-control robot, comprising:
a base component;
a mobile platform arranged proximate said base component;
a translation assembly operatively connected to said base component and said mobile platform and configured to move said mobile platform with translational degrees of freedom substantially without rotation with respect to said base component;
a tool assembly connected to said mobile platform, wherein said tool assembly comprises a tool holder and a tool rotation assembly connected to said tool holder;
a control system configured to communicate with said translation assembly to control motion of said mobile platform in response to forces by a user applied to at least a portion of said cooperative-control robot; and
at least one force sensor attached to said holder,
wherein said translation assembly comprises at least three independently operable actuator arms, each connected to a separate position of said mobile platform,
wherein said tool rotation assembly provides at least two rotational degrees of freedom for orienting said tool when held by said tool holder, and
wherein said at least one force sensor detects at least one force component applied by said user to said tool when held by said tool holder causing said control system to move said mobile platform and said tool assembly a desired way.

2. A cooperative-control robot according to claim 1, wherein said translation assembly further comprises at least three motors, each operably connected to a respective one of said at least three independently operable actuator arms,
wherein each of said at least three motors is supported by said base component such that said mobile platform is free to move without carrying weight of said motors.

3. A cooperative-control robot according to claim 1, wherein each of said at least three independently operable actuator arms comprises a pair of interconnected structural members arranged to form a parallelogram shape which is variable in skewness during operation.

4. A cooperative-control robot according to claim 1, wherein said at least three independently operable actuator arms are articulated arms.

5. A cooperative-control robot according to claim 3, wherein said at least three independently operable actuator arms are articulated arms.

6. A cooperative-control robot according to claim 1, wherein said translation assembly further comprises at least three linear tracks arranged such that each of said at least three independently operable actuator arms has an end that is constrained to move along a respective one of said at least three linear tracks.

7. A cooperative-control robot according to claim 6, wherein said at least three linear tracks are at least one of attached to, or integral with, said base component.

8. A cooperative-control robot according to claim 1, wherein said base component is adapted to be mountable to an overhead boom.

9. A cooperative-control robot according to claim 1, wherein said base component is adapted to be mountable to a bedrail.

10. A cooperative-control robot according to claim 7, wherein said base component is adapted to be mountable to an overhead boom.

11. A cooperative-control robot according to claim 7, wherein said base component is adapted to be mountable to a bedrail.

12. A cooperative-control robot according to claim 1, wherein said force sensor is a six-degree-of-freedom force sensor.

13. A robotic system, comprising:
a support structure;
first and second cooperative-control robots connected to said support structure; and
a control system adapted to communicate with said first and second cooperative-control robots,
wherein each of said first and second cooperative-control robots comprises:
a base component connected to said support structure,
a mobile platform arranged proximate said base component,
a translation assembly operatively connected to said base component and said mobile platform and configured to move said mobile platform with translational degrees of freedom substantially without rotation With respect to said base component, and
a tool assembly connected to said mobile platform,
wherein said control system is configured to control motion of each said mobile platform in response to forces by a user applied to at least a portion of a corresponding one of said first and second cooperative-control robots,
wherein each said translation assembly comprises at least three independently operable actuator arms, each connected to a separate position of said mobile platform,
wherein said tool assembly comprises a tool holder and a tool rotation assembly connected to said tool holder,
wherein said tool rotation assembly provides at least two rotational degrees of freedom for orienting said tool when held by said tool holder, and
wherein at least one force sensor attached to said tool holder detects at least one force component applied by said user to said tool when held by said tool holder causing said control system to move said mobile platform and said tool assembly a desired way.

14. A robotic system according to claim 13, wherein said support structure comprises a first overhead boom.

15. A robotic system according to claim 14, wherein said support structure comprises a second overhead boom rotatably attached to the first overhead boom.

16. A robotic system according to claim 13, wherein said support structure comprises a first bedrail.

17. A robotic system according to claim 16, wherein said support structure comprises a second bedrail, and
wherein said first cooperative-control robot is connected to the first-mentioned bedrail and said second cooperative-control robot is connected to said second bedrail.

18. A robotic system according to claim 13, further comprising a user input device adapted to communicate with said control system to at least one of interrupt or supplement cooperative control due to said forces applied by said user.

19. A robotic system according to claim 18, wherein said user input device is a foot pedal.

20. A cooperative-control robot according to claim 1, wherein said control system moves said mobile platform and said tool assembly said desired way in a smooth manner in response to said forces by said user.

21. A robotic system according to claim 13, wherein said control system moves said mobile platform and said tool assembly said desired way in a smooth manner in response to said forces by said user.

22. A robotic system according to claim 13, wherein said translation assembly further comprises at least three linear tracks arranged such that each of said at least three independently operable actuator arms has an end that is constrained to move along a respective one of said at least three linear tracks.

23. A robotic system according to claim 22, wherein said at least three linear tracks are at least one of attached to, or integral with, said base component.

* * * * *